United States Patent
Steiner et al.

(10) Patent No.: US 6,900,355 B2
(45) Date of Patent: *May 31, 2005

(54) PROCESS FOR THE CIS-SELECTIVE CATALYTIC HYDROGENATION OF CYCLOHEXYLIDENAMINES

(75) Inventors: Heinz Steiner, Bubendorf (CH); Marc Thommen, Nuglar (CH); Hans-Peter Jalett, Dornach (CH); Markus Benz, Arlesheim (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/794,758

(22) Filed: Mar. 5, 2004

(65) Prior Publication Data

US 2004/0171883 A1 Sep. 2, 2004

Related U.S. Application Data

(63) Continuation of application No. 10/031,882, filed as application No. PCT/EP00/06932 on Jul. 20, 2000, now Pat. No. 6,720,454.

(30) Foreign Application Priority Data

Jul. 29, 1999 (CH) .............................................. 1399/99

(51) Int. Cl.$^7$ ............................................ C07C 211/00
(52) U.S. Cl. ........................ 564/308; 564/446; 564/448
(58) Field of Search ................................ 564/308, 446, 564/448

(56) References Cited

U.S. PATENT DOCUMENTS

| | | | | |
|---|---|---|---|---|
| 4,536,518 A | 8/1985 | Welch et al. | ................ | 514/647 |
| 6,232,501 B1 | 5/2001 | Steiner et al. | .............. | 564/308 |
| 6,720,454 B1 * | 4/2004 | Steiner et al. | .............. | 564/308 |

FOREIGN PATENT DOCUMENTS

| | | |
|---|---|---|
| EP | 0030081 | 6/1981 |
| WO | 93/01161 | 1/1993 |
| WO | 93/12062 | 6/1993 |
| WO | 98/27050 | 6/1998 |
| WO | 99/47486 | 9/1999 |

OTHER PUBLICATIONS

Cossy et al., Tetrahedron (1999) vol. 55, No. 21, p. 6483–6496.*
R. Sarges, Journal of Organic Chemistry, US, American Chemical Society, vol. 40, No. 9, (1975), pp. 1216–1224.
R.B.C. Pillai, Journal of Molecular Catalysis, vol. 84, (1993), pp. 125–129.
Dovell et al., Industrial & Engineering Chemistry Product Research and Development, Copper Chromite Catalysts for Reductive Alkylation, 1962, 1, pp. 179–181.

* cited by examiner

*Primary Examiner*—Brian Davis
(74) *Attorney, Agent, or Firm*—Kevin T. Mansfield

(57) ABSTRACT

The invention relates to a process for the cis-selective preparation of cyclic amines of the sertralin type by reductive alkylation of cyclic imines or their precursors and catalytic hydrogenation in the presence of copper-containing catalysts and in the presence of a protic solvent.

7 Claims, No Drawings

PROCESS FOR THE CIS-SELECTIVE CATALYTIC HYDROGENATION OF CYCLOHEXYLIDENAMINES

This application is a continuation of application Ser. No. 10/031,882 filed Jan. 25, 2002, now U.S. Pat. No. 6,720,454, which is the 371 National Stage of International Application No. PCT/EP00/06932, filed Jul. 20, 2000.

The invention relates to a process for the cis-selective catalytic hydrogenation of cyclohexylidenamines and their precursors.

Cyclohexylamines can be used, inter alia, as antioxidants and as active ingredients in pharmaceuticals. An important cyclohexylamine is sertralin:

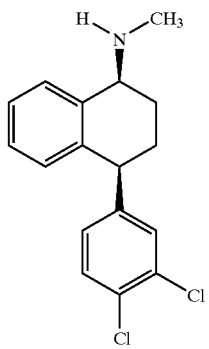

Sertraline: (1S,4S)-4-(3,4-dichlorophenyl)-1,2,3,4-tetrahydro-N-methyl-1-napthylamine, cf. *Merck Index Twelfth Edition* 1996, No. 8612 is known as an antidepressant. The preparation of this compound is described in U.S. Pat. No. 4,536,518. The hydrochloride is commercially available, inter alia, under the trade names Lustral® and Zoloft®. Cyclohexylamines of the type:

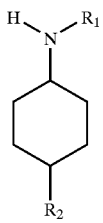

($R_2 \neq H$) exist in at least two isomeric forms:

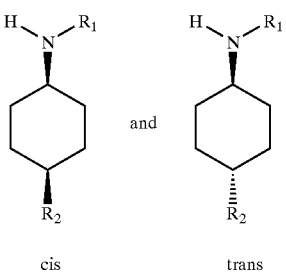

cis          trans

In the case of further, asymmetric substitution on the cyclohexyl ring, the carbon atoms in the 1 and 4 positions are chiral. According to the R,S nomenclature of *Kahn, Ingold and Prelog*, sertralin has the 1S, 4S configuration.

Cyclohexylamines are obtained, for example, by the following method: reaction of the ketone:

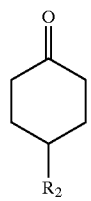

with a primary amine, e.g. methylamine, results in elimination of water to give a cyclohexylidenamine:

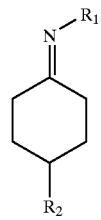

The imine formed is subsequently catalytically hydrogenated to give the amine. Such reactions proceed in only a low stereoselectivity, if any. In the case of sertralin, four enantiomers are obtained.

It is an object of the present invention to prepare cyclohexylamines containing a very high proportion of cis-isomers.

To achieve the object, the abovementioned U.S. Pat. No. 4,536,518, for example, proposes hydrogenating an imine of the formula:

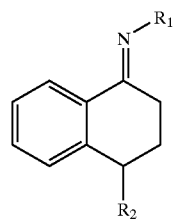

$R_2$ = 3,4-Dichlorophenyl using palladium on carbon as support. This gives 70% of cis-racemate and 30% of trans-racemate.

To improve this yield further, WO 93/01161 proposes using Raney nickel as catalyst in place of palladium on carbon as support for the hydrogenation of the imine. This gives a cis/trans ratio of 8:1.

It has now surprisingly been found that an even better cis/trans ratio is obtained when the imine is hydrogenated in the presence of a copper-containing catalyst and in the presence of a protic solvent. Although the preparation of secondary amines from ketones and intermediate imines by hydrogenation in the presence of copper chromite catalysts is known from R. B. C. Pillai *J. Mol. Catalysis* 84 (1993), 125–129, it is surprising that when starting from cyclohexylidenamines, which can also be formed as intermediates from ketones, the hydrogenation using a copper-containing catalyst proceeds diastereoselectively and gives a high proportion (>95%) of cis isomers.

The invention provides a process for preparing cis compounds of the formula:

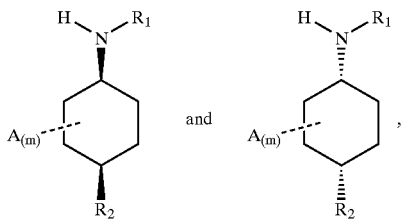 (I)

in which $R_1$ and $R_2$ are, independently of one another, hydrocarbon radicals and A are substituents and m is an integer from 0 to 4 which defines the number of substituents A, which comprises a) hydrogenating a cyclohexylidenamine of the formula:

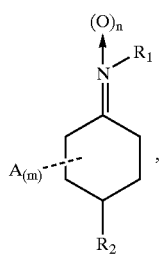 (II)

in which n is zero or 1, $R_1$, $R_2$, A and m are as defined above, in the presence of a copper-containing catalyst and in the presence of a protic solvent; or b) reacting a ketone of the formula:

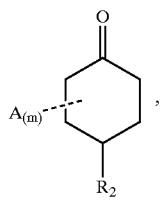 (III)

in which $R_2$, A and m are as defined above, with a compound which introduces the group $R_1$—N→$(O)_n$, hydrogenating the imine or nitrone (II) obtainable as an intermediate in the presence of a copper-containing catalyst and in the presence of a protic solvent and isolating the cis compound (I).

When m is zero and the cyclohexyl ring is unsubstituted in a compound (I), the two structural formulae represent identical compounds:

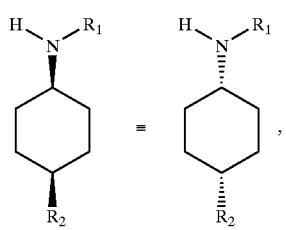 (I)

In the description of the present invention, the structural formula of the cis compound (I) of both possibilities is represented using only the formula:

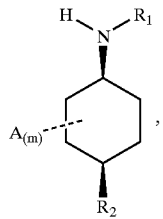 (III)

When m is from 1 to 4 (m>0) and the cyclohexyl ring is unsymmetrically substituted in a compound (1), the hydrogenation selectively gives a cis enantiomer pair which can be separated into the optically pure enantiomers by customary methods of racemate resolution, for example by crystallization of the mandelic acid salt using the method of W. M. Welch et al in *J. Med. Chem.* 1984, 27, 1508–1515. The relationship between the two cis and trans enantiomer pairs and the four optically pure enantiomers is illustrated by the following formulae for sertraline:

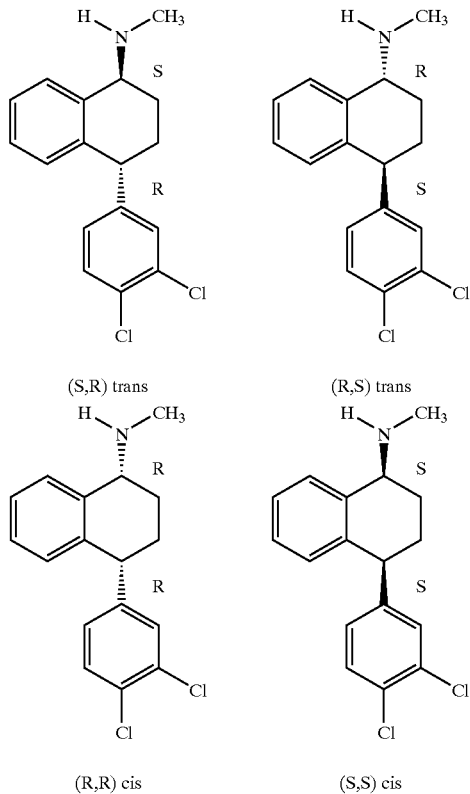

In the structural formulae of the starting materials (II) and (III), the uniform-thickness bonds to the substituent $R_2$ indicate that in the case of $R_2 \neq H$ and different substitution on the cyclohexyl ring, these starting materials can be used in the process in the form of racemic mixtures having equal or different proportions of the enantiomers or in the form of an optically pure enantiomer.

The process gives a high yield of desired cis compounds. In the case of the synthesis of sertralin, a ratio of the cis enantiomer pair to the trans enantiomer pair of greater than 95:5 is obtained. In a particularly preferred embodiment, the even better ratio of greater than 99:1 is achieved. This high yield of cis compounds also eliminates the separation of the cis enantiomer pair from the trans enantiomer pair which is otherwise necessary in the presence of different substituents A (m>0).

The definitions and designations used in the description of the present invention preferably have the following meanings:

A hydrocarbon radical $R_1$ or $R_2$ is selected, in particular, from the group consisting of $C_1-C_{20}$alkyl, $C_4-C_{12}$cycloalkyl, $C_2-C_{11}$heterocycloalkyl, carbocyclic $C_5-C_{16}$aryl, $C_2-C_{15}$heteroaryl, carbocyclic $C_7-C_{16}$aralkyl and $C_2-C_{15}$heteroarylalkyl and can additionally be substituted by a suitable functional group, e.g. selected from the group of functional groups or derivatized functional groups consisting of amino, $C_1-C_4$alkylamino, $C_1-C_4$dialkylamino, hydroxy, carboxy and halogen.

The cyclohexyl ring can be substituted by from one to four, preferably two, substituents selected from the group A consisting of the substituents $R_3$, $R_4$, $R_5$ and $R_6$. Suitable substituents are listed in the *List of Radical Names* under the *IUPAC Rules* and remain unchanged under the conditions of the catalytic hydrogenation reaction. The substituents may be chosen freely. Suitable substituents A from the group $R_3$, $R_4$, $R_5$ and $R_6$ are, for example, selected from the group of functional groups or derivatized functional groups consisting of amino, $C_1-C_4$alkylamino, $C_1-C_4$dialkylamino, hydroxy, carboxy and halogen or are saturated aliphatic, cycloaliphatic or heterocycloaliphatic radicals, carbocyclic or heterocyclic aryl radicals, fused carbocyclic, heterocyclic or carbocyclic-heterocyclic radicals, which may in turn be combined in any way with further radicals of this group and can be substituted by the functional groups or derivatized functional groups mentioned.

The abovementioned substituents and radicals can also be interrupted by one or more divalent radicals selected from the group consisting of —O—, —C(=O)—O—, —O—C(=O)—, —C(=O)—N($C_1-C_4$alkyl)-, —N($C_1-C_4$alkyl)-C(=O)—, —S(=O)$_2$—, —S(=O)$_2$—O—, —O—S(=O)$_2$—, —S(=O)$_2$—N($C_1-C_4$alkyl)-, —($C_1-C_4$alkyl)N—S(=O)$_2$—, —P(=O)—, —P(=O)—O—, —O—P(=O)— and —O—P(=O)—O—.

In a preferred embodiment, two substituents A from the group $R_3$, $R_4$, $R_5$ and $R_6$ form divalent, bridging $C_2-C_6$alkylene, $C_4-C_8$alkyldiylidene or $C_4-C_8$alkenyldiylidene groups, preferably butanediylidene, in particular 2-butenediylidene which is joined to the cyclohexyl ring at two adjacent carbon atoms and together with these carbon atoms forms a phenyl ring which may be substitued by the abovementioned functional groups or substituents.

Further suitable substituents A from the group $R_3$, $R_4$, $R_5$ and $R_6$ are substituents selected from the group consisting of $C_1-C_{20}$alkyl, $C_4-C_{12}$cycloalkyl, $C_7-C_{12}$bicycloalkyl, $C_2-C_{11}$heterocycloalkyl, carbocyclic $C_6-C_{16}$aryl, $C_2-C_{15}$heteroaryl, carbocyclic $C_7-C_{16}$aralkyl and $C_2-C_{15}$heteroarylalkyl, which may in turn be substituted by the abovementioned functional groups and interrupted by divalent radicals.

Examples of $C_1-C_{20}$alkyl are methyl, ethyl, n-propyl or isopropyl and n-, sec- or tert-butyl and also straight-chain or branched pentyl, hexyl, heptyl, octyl, isooctyl, nonyl, tert-nonyl, decyl, undecyl or dodecyl.

Examples of $C_4-C_{12}$cycloalkyl are cyclopropyl, dimethylcyclopropyl, cyclobutyl, cyclopentyl and cyclohexyl.

Examples of $C_7-C_{12}$bicycloalkyl are bornyl and norbornyl.

$C_2-C_{11}$heterocycloalkyl preferably contains 4 or 5 carbon atoms and one or two heteroatoms selected from the group consisting of O, S and N. Examples are the substituents derived from oxirane, azirine, 1,2-oxathiolane, pyrazoline, pyrrolidine, piperidine, piperazine, morpholine, tetrahydrofuran or tetrahydrothiophene.

Carbocyclic $C_6-C_{16}$aryl is, for example, monocyclic, bicyclic or tricyclic, e.g. phenyl, naphthyl, indenyl, azulenyl or anthryl.

$C_1-C_{15}$heteroaryl is preferably monocyclic or fused to a further heterocycle or an aryl radical, e.g. phenyl, and preferably contains one or two, in the case of nitrogen up to four, heteroatoms selected from the group consisting of O, S and N. Suitable substituents are derived from furan, thiophene, pyrrole, pyridine, bipyridine, picoline, γ-pyran, γ-thiopyran, phenanthroline, pyrimidine, bipyrimidine, pyrazine, indole, cumarone, thionaphthene, carbazole, dibenzofuran, dibenzothiophene, pyrazole, imidazole, benzimidazole, oxazole, thiazole, dithiazole, isoxazole, isothiazole, quinoline, isoquinoline, acridine, chromene, phenazine, phenoxazine, phenothiazine, triazine, thianthrene, purine or tetrazole.

Carbocyclic $C_7-C_{16}$aralkyl preferably contains from 7 to 12 carbon atoms, e.g. benzyl, 1- or 2-phenethyl or cinnamyl.

$C_2-C_{15}$heteroarylalkyl preferably consists of the abovementioned heterocycles substituting, for example, $C_1-C_4$alkyl radicals, depending on the length of the carbon chain preferably at the end, but also in the adjacent position (1 position) or in the α position (2 position).

In a preferred embodiment, a cis enantiomer pair of the compound of the formula:

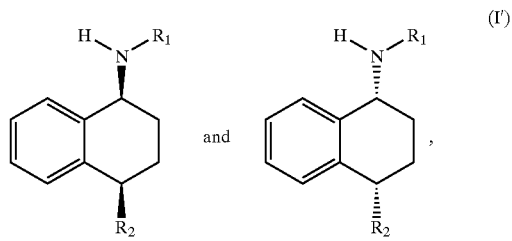

in which $R_1$ is $C_1-C_4$alkyl and $R_2$ is aryl, is prepared.

In process variant a), a cyclohexylidenamine, or the imine or nitrone (II), in particular the imine or nitrone of the formula:

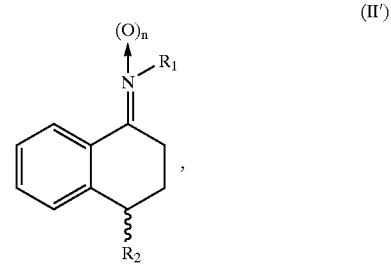

in which $R_1$ and $R_2$ are as defined above and which can be in the syn or anti form, is hydrogenated in the presence of a copper-containing catalyst and in the presence of a protic solvent.

In process variant b), a ketone (III), in particular a ketone of the formula

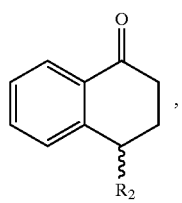
(III')

in which $R_2$ is as defined above, is reacted with a compound which introduces the group $R_1-N \rightarrow (O)_n$, in particular a primary amine, preferably methylamine, or an $R_1$-substituted hydroxylamine, in particular N-methylhydroxylamine, and the imine (II) obtainable as an intermediate is hydrogenated in-situ in the presence of a copper-containing catalyst and in the presence of a protic solvent. Instead of a racemic compound (II') or (III'), it is also possible to use an optically pure compound (II') or (III') and convert this into a cis compound (I').

The invention preferably provides a process for preparing the cis compound (I') in which $R_1$ is methyl and $R_2$ is 3,4-dichlorophenyl, which comprises a) hydrogenating an imine or nitrone (II') in which $R_1$ is methyl and $R_2$ is 3,4-dichlorophenyl in the presence of a copper-containing catalyst and in the presence of a protic solvent or b) reacting a ketone (III') in which $R_2$ is 3,4-dichlorophenyl with methylamine or N-methylhydroxylamine, hydrogenating the imine or nitrone (II) obtainable as an intermediate in the presence of a copper-containing catalyst and in the presence of a protic solvent and isolating the cis compound (I').

Suitable catalysts for the hydrogenation reaction in variants a) and b) are copper-containing catalysts, e.g. skeletal copper catalysts, supported copper catalysts, copper chromite catalysts, copper-zinc oxide catalysts, copper boride catalysts or Urushibara copper catalysts.

In a preferred embodiment of the process, further elements in addition to copper are present in the catalyst. Examples are aluminium, chromium, zinc, barium, manganese, zirconium, vanadium, molybdenum, titanium, tantalum, niobium, tungsten, nickel, cobalt, bismuth, tin, antimony, hafnium, rhenium, iron, cadmium, lead and germanium and mixtures thereof. The amount of the element added can vary within wide limits. It can be in the range from 10 ppm to 200%, based on the amount of copper used. Particularly suitable elements are aluminium, zinc, chromium, barium and manganese. The elements can, for example, be present in the form of oxides or salts such as chromates.

Raney copper is an example of a suitable skeletal copper catalyst.

Examples of supports are carbon, aluminium oxide, silicon dioxide, $Cr_2O_3$, zirconium dioxide, zinc oxide, calcium oxide, magnesium oxide, barium sulfate, calcium carbonate and aluminium phosphate. The copper can be present in an amount of about 1.0–20.0% by weight bound to the support.

A suitable copper chromite catalyst has the empirical formula $CuO \cdot CuCr_2O_4$. $CuCr_2O_4$ is known, cf. C.A.R.N. 12018-10-9 and *Gmelins Handbuch der Anorganischen Chemie*, $8^{th}$ edition, Volume Copper, Part B, Issue 3, System number 60, page 60. Another customary designation is copper(II) chromate(III). Copper chromite catalysts having varying proportions of CuO and $CuCr_2O_4$, Raney copper catalysts and copper-zinc-aluminium oxide catalysts are commercially available in pure form or in a form doped with the abovementioned elements.

In a preferred embodiment of the process, the copper-containing catalysts used are copper chromite catalysts or catalysts comprising copper, zinc, barium and aluminium in the form of oxides.

The catalysts mentioned are present in the reaction mixture in an amount of from about 0.1 to 100% by weight, in particular 1–20% by weight, based on the amount of starting material used.

The copper-containing catalysts can be used in the process in various ways:

in the form of ready-to-use catalysts;

in the form of prehydrogenated catalysts or in the form of catalysts prepared in situ from suitable precursors, e.g. copper salts or oxides, and further compounds.

The prehydrogenation can, for example, be carried out by treating a suspension of the catalyst in a suitable solvent under from 5 to 150 bar of hydrogen at 80–250° C. for from half an hour to 5 hours, or by passing hydrogen over the dry catalyst at from atmospheric pressure to 50 bar at from 100 to 500° C.

In a preferred embodiment of the process, the catalyst used is activated by hydrogenation in the solvent which is used for the hydrogenation of the imine or nitrone ("prehydrogenation"). After the hydrogenation, the catalyst can be separated off, for example, by filtration when the process is carried out batchwise.

Imines (II) can be prepared by reaction of ketones (II) with a compound which introduces the group $R_1-N$, in particular a primary amine, preferably methylamine. The preparation of imines (II) is carried out by a method analogous to that described in U.S. Pat. No. 4,536,518.

Nitrones (II) can be prepared by reaction of ketones (II) with a compound which introduces the group $R_1-N \rightarrow O$, e.g. $R_1$-substituted hydroxylamine, in particular N-methylhydroxylamine. The preparation of nitrones (II) is carried out by a method analogous to that described in WO 98/27050.

The hydrogenation is carried out in the presence of a protic organic solvent. Suitable protic solvents are, for example, monohydric and polyhydric alcohols, preferably $C_1–C_5$ monoalcohols such as isopropanol, n-butanol, methanol or very particularly preferably ethanol. Mixtures of various protic solvents can also be used.

In variant b), acidic auxiliaries, e.g. organic monobasic or polybasic acids having more than two carbon atoms, e.g. acetic acid, propionic acid or malonic acid, mineral acids such as sulfuric acid, Lewis acids, e.g. boron trifluoride, or solid acids such as zeolites or Nafion® and/or desiccants such as sodium sulfate may be added if desired.

In variant b), an excess of up to 50 mol of the amine used, e.g. methylamine in the form of methylamine gas or as a solution, e.g. in ethanol, is added.

In both variants, the process can advantageously be carried out in the liquid phase, either batchwise or continuously, in particular using a catalyst suspension as a liquid-phase hydrogenation or in a bubble column or using a shaped catalyst in a trickle bed. The reaction can also be carried out in the gas phase using a pulverulent catalyst in a fluidized bed or using a shaped catalyst in a fixed bed.

The hydrogenation can be carried out within a wide temperature range. Temperatures of from 60° C. to about 250° C., in particular from 90° to 150° C., have been found to be advantageous.

The hydrogen pressure in the hydrogenation can vary within wide limits, e.g. 1–100 bar, preferably 5–50 bar, in particular 10–20 bar. The hydrogen pressure employed depends essentially on the hydrogenation facility available. In place of molecular hydrogen, it is also possible to use a hydrogen donor such as isopropanol at relatively high temperatures of about 100° C.

The reaction time can vary within wide limits. It depends on the catalyst used, on the hydrogen pressure, on the reaction temperature and on the hydrogenation facility used. It can be, for example, from half an hour to 24 hours. Reaction times of from about half an hour to two hours are advantageous.

The isolation of the reaction products is carried out by known methods and is described in the examples. Removal of the catalyst and the solvent can be followed by the customary separation methods, e.g. preparative thin layer chromatography, preparative HPLC, preparative gas chromatography, etc. The cis racemate obtained from racemic cyclohexylidenamine can, without further purification, be resolved into the optically pure enantiomers by means of the known methods of separating enantiomers, e.g. by means of preparative chromatography over chiral supports (HPLC) or by precipitation or crystallization using optically pure precipitants, e.g. using D-(+)- or L-(−)-mandelic acid or (+)- or (−)-10-camphorsulfonic acid. When enantiomerically pure 4-substituted cyclohexylidenamine is used as starting material, the hydrogenation process of the invention gives the enantiomerically pure 4-substituted cyclohexylamine directly.

The invention likewise provides for the use of copper-containing catalysts for the diastereoselective hydrogenation of cyclohexylidenamines. Preference is given to using copper chromite catalysts, CuCrBa oxide or CuZnAl oxide catalysts for the diastereoselective hydrogenation of cyclohexylidenamines.

The following examples illustrate the invention:

EXAMPLE 1

The prehydrogenated catalyst (CuCrBa oxide, 2% based on imine starting material) is placed in an autoclave, 15 g of 4-(3,4-dichlorophenyl)-1-methylimino-1,2,3,4-tetrahydronaphthalene are added and the mixture is covered with 30 ml of ethanol.

The autoclave is closed and the air is replaced by nitrogen. The nitrogen is subsequently replaced by hydrogen and an initial pressure of 12 bar of hydrogen is set and the stirrer is switched on. The autoclave is then heated to 130° C. and commencement of the reaction can be observed above 90° C. After a temperature of 130° C. has been reached, the reaction takes about 45 minutes–1 hour until hydrogen absorption ceases. The hydrogenation time is 20 minutes. The autoclave is subsequently cooled, the catalyst is filtered off and the solution is evaporated on a rotary evaporator.

The cis/trans ratio of the 4-(3,4-dichlorophenyl)-1,2,3,4-tetrahydro-N-methyl-1-naphthylamine obtained is determined by means of HPLC: 99.6:0.4.

Yield: 86% of the theoretical yield of pure cis racemate.

EXAMPLE 2

The procedure described in Example 1 is repeated, except that the hydrogenation is carried out at 150° C. (instead of 130° C.). The hydrogenation time is still about 20 minutes.

Cis/trans ratio of the 4-(3,4-dichlorophenyl)-1,2,3,4-tetrahydro-N-methyl-1-naphthylamine obtained: 98.8:1.2

Yield: 83% of the theoretical yield of pure cis racemate.

EXAMPLE 3

The procedure described in Example 1 is repeated, except that the catalyst concentration is 7%, based on the imine.

Cis/trans ratio of the 4-(3,4-dichlorophenyl)-1,2,3,4-tetrahydro-N-methyl-1-naphthylamine obtained: 97:3.

Yield: 85% of the theoretical yield of pure cis racemate.

EXAMPLES 4 to 6

The procedure described in Example 1 is repeated, except that the 30 ml of ethanol is replaced by an equal amount of methanol, isopropanol or n-butanol.

What is claimed is:

1. A process for preparing compounds of the formula

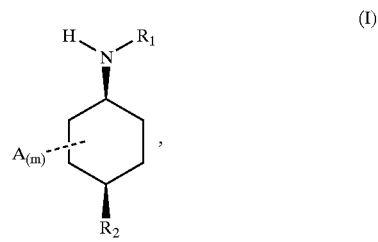

(I)

in which $R_1$ and $R_2$ are, independently of one another, hydrocarbon radicals and A are substituents and m is an integer from 0 to 4 which defines the number of substituents A, which comprises a) hydrogenating a cyclohexylidenamine of the formula:

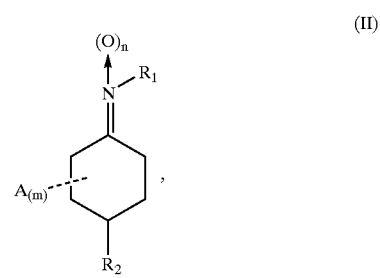

(II)

in which n is zero or 1, $R_1$, $R_2$, A and m are as defined above, in the presence of a copper-containing catalyst and in the presence of a protic solvent; or b) reacting a ketone of the formula:

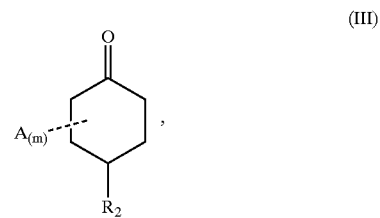

(III)

in which $R_2$, A and m are as defined above, with a compound which introduces the group $R_1$—N→$(O)_n$, hydrogenating the imine or nitrone (II) obtainable as an intermediate in the presence of a copper-containing catalyst and in the presence of a protic solvent and isolating the cis compound (I).

2. A process for preparing compounds of the formula I according to claim 1 in which the hydrocarbon radicals $R_1$ or $R_2$ are selected from the group consisting of $C_1$–$C_{20}$alkyl, $C_4$–$C_{12}$cycloalkyl, $C_4$–$C_{12}$cycloalkenyl, $C_2$–$C_{11}$heterocycloalkyl, carbocyclic $C_6$–$C_{16}$aryl, $C_2$–$C_{15}$heteroaryl, carbocyclic $C_7$–$C_{16}$aralkyl and $C_2$–$C_{15}$heteroarylalkyl and are substituted by functional groups from the group consisting of amino, $C_1$–$C_4$alkylamino, $C_1$–$C_4$dialkylamino, hydroxy, carboxy and halogen, m is two and A are substituents $R_3$ and $R_4$ which are independently or together saturated aliphatic, cycloaliphatic or heterocycloaliphatic radicals or carbocyclic, heterocyclic or carbocyclic-heterocyclic radicals which may be combined in any way with further radicals of this type or be substituted by functional groups from the group consisting of amino, $C_1$–$C_4$alkylamino, $C_1$–$C_4$dialkylamino, hydroxy, carboxy and halogen, which comprises a) carrying out the process variant a) using a correspondingly substituted imine (II) in which m is 2 and $R_1$, $R_2$, $R_3$ and $R_4$ are as defined above, or b) carrying out the process variant b) using a correspondingly substituted ketone (III) in which m is 2 and $R_3$ and $R_4$ are as defined above.

3. A process according to claim 1 for preparing the cis enantiomer pair of the compound of the formula

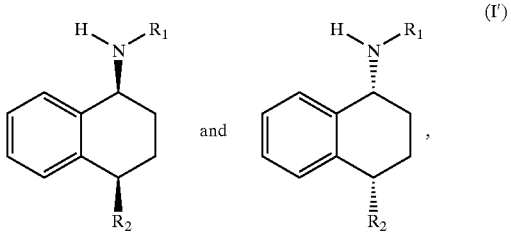
(I')

in which $R_1$ is $C_1$–$C_4$alkyl and $R_2$ is aryl, wherein a) an imine or nitrone of the formula

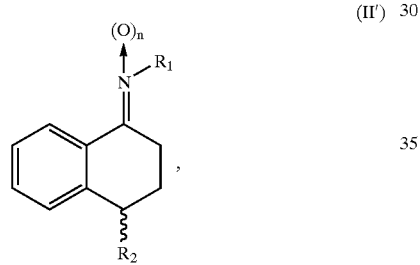
(II')

in which $R_1$ is methyl and $R_2$ is 3,4-dichlorophenyl, is hydrogenated in the presence of a copper-containing catalyst and in the presence of a protic solvent; or a ketone of the formula

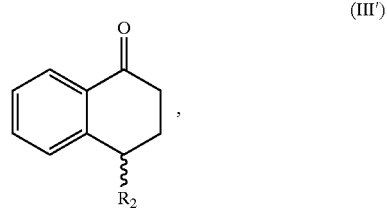
(III')

in which $R_2$ is as defined above, is reacted with a compound which introduces the group $R_1$—N, the imine or nitrone (II) obtainable as an intermediate is hydrogenated in situ in the presence of a copper-containing catalyst and in the presence of a protic solvent and the compound (I') is isolated.

4. A process according to claim 3 for preparing the cis compound (I') in which $R_1$ is methyl and $R_2$ is 3,4-dichlorophenyl, wherein a) an imine or nitrone (II') in which $R_1$ is methyl and $R_2$ is 3,4-dichlorophenyl is hydrogenated in the presence of a copper-containing catalyst and in the presence of a protic solvent or b) a ketone (III') in which $R_2$ is 3,4-dichlorophenyl is reacted with methylamine or N-methylhydroxylamine, the imine or nitrone (II) obtainable as an intermediate is hydrogenated in the presence of a copper-containing catalyst and in the presence of a protic solvent and the cis compound (I') is isolated.

5. A process according to claim 1, wherein the compound (I) is prepared by hydrogenation in the presence of a copper chromite, CuCrBa oxide or CuZnAl oxide catalyst.

6. A process according to claim 1, wherein the protic solvent used is a monohydric or polyhydric alcohol.

7. A process according to claim 6, wherein the protic solvent used is a $C_1$–$C_5$monoalcohol.

* * * * *